United States Patent [19]
Fischer

[11] 3,969,101
[45] July 13, 1976

[54] AGENT FOR CONTROLLING PLANT GROWTH

[75] Inventor: Hanspeter Fischer, Bottmingen, Switzerland

[73] Assignee: Ciba-Geigy Corporation, Ardsley, N.Y.

[22] Filed: Mar. 5, 1974

[21] Appl. No.: 448,438

Related U.S. Application Data

[62] Division of Ser. No. 252,385, May 11, 1972, abandoned.

[30] Foreign Application Priority Data

May 17, 1971  Switzerland........................ 7229/71

[52] U.S. Cl........................................ 71/92; 71/72; 71/76; 71/78; 71/86; 71/88; 71/95; 260/239 E; 260/239 B; 260/247.1 M; 260/256.4 N; 424/251

[51] Int. Cl.².......................................... A01N 9/22

[58] Field of Search....................................... 71/92

[56] References Cited
UNITED STATES PATENTS

| | | | |
|---|---|---|---|
| 3,118,754 | 1/1964 | Nickell................................... | 71/92 |
| 3,126,271 | 3/1964 | Thomson et al....................... | 71/92 |
| 3,169,848 | 2/1965 | Gysin et al............................. | 71/92 |
| 3,461,461 | 8/1969 | Anthony et al................. | 260/256.4 |
| 3,806,333 | 4/1974 | Ayad...................................... | 71/92 |
| 3,892,554 | 7/1975 | Schneider.............................. | 71/92 |

OTHER PUBLICATIONS
Brown et al., J. Chem. Soc., 1965, pp. 3770–3778.

*Primary Examiner*—Glennon H. Hollrah
*Attorney, Agent, or Firm*—Harry Falber

[57] ABSTRACT

2-Alkylthio-4,6-bis(subst.amino)-5-nitropyrimidines are agents effectively influencing plant metabolism. They can be employed as preemergence herbicides.

14 Claims, No Drawings

AGENT FOR CONTROLLING PLANT GROWTH

This is a division of application Ser. No. 252,385, filed on May 11, 1972, now abandoned.

The present invention relates to pyrimidine derivatives and to processes for their production, as well as to agents regulating plant growth which contain these pyrimidine derivatives as active substances.

Certain 2,4-bis(subst.amino)-pyrimidines are described in the French Patent No. 1,572,620 as fungicides and insecticides. In the Dutch Patent No. 68.14057, substituted pyrimidines are mentioned which have fungicidal activity against, in particular, phytopathogenic fungi on fruit and vegetable plants.

Surprisingly, it has now been found that the new 5-nitropyrimidines of formula I, as well as their addition salts or their salts obtained by quaternation, have the property of regulating plant metabolism, without noticeably having any detrimental herbicidal effect on emergeed plants.

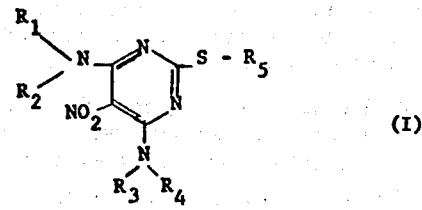

(I)

The symbols in this formula have the following meanings:

$R_1$ represents an alkyl radical having 2 to 6 carbon atoms, an alkenyl radical or alkinyl radical having 3 to 5 carbon atoms, an alkoxyalkyl, alkylaminoalkyl, trialkylammonioalkyl radical, a hydroxyalkyl or cyanoalkyl radical having 1 to 4 carbon atoms, a cycloalkyl radical having 3 to 6 carbon atoms, $R_2$ and $R_3$ each independently represent hydrogen, or a lower alkyl radical, $R_4$ represents hydrogen, a lower alkyl radical, a cycloalkyl radical having 3 to 6 carbon atoms, and the pairs of symbols $R_1$ and $R_2$ and/or $R_3$ and $R_4$ furthermore together represent a polymethylene bridge member in which a methylene group can be replaced by oxygen, nitrogen, or the group $>N - R'$ wherein $R'$ stands for a lower alkyl radical, and $R_5$ represents a lower alkyl radical.

By alkyl radicals or by lower alkyl radicals in formula I are meant straight-chain or branched radicals having 1 to 6 carbon atoms, such as, e.g. methyl, ethyl, n-propyl, isopropyl, n-butyl, isobutyl, sec.butyl, tert.butyl, n-pentyl, n-hexyl, and the isomers of the $C_5$- and $C_6$-alkyl radicals. The lower straight-chain or branched alkyl radicals having 1 to 6 or 2 to 6 carbon atoms form moreover the alkyl moiety of alkoxy, alkylthio, dialkylamino, alkylamino, trialkylammonio substituents. Alkenyl radicals in formula I are straight-chain or branched radicals having 3 to 5 carbon atoms, e.g. propenyl, butenyl and pentenyl radicals; preferred radicals are the allyl, methallyl, 3-methylbutenyl or n-butenyl radicals. Alkinyl radicals preferably contain 3 to 5 carbon atoms in a straight chain; propinyl and butinyl radicals are preferred such as the 2-propinyl radical, or a propinyl radical substituted by lower alkyl. To be mentioned as cycloalkyl radicals having 3 to 6 ring carbon atoms are, e.g. cyclopropyl, cyclobutyl, cyclopentyl and cyclohexyl. These rings can be substituted by methyl or ethyl.

A heterocycle formed by the symbol-pairs $R_1/R_2$ and $R_3/R_4$ with the adjacent nitrogen atom contains 3 to 7 and 5 to 7 ring members, respectively. Such heterocycles are, for example, aziridine, pyrrolidine, piperidine, hexahydroazepine, piperazine, N-methylpiperazine and N-phenylpiperazine, or morpholine.

By addition salts are meant the salts with inorganic or organic strong acids, preferably hydrochloric acid, hydrobromic acid, phosphoric acid, sulphuric acid, nitric acid, fluoroboric acid ($HBF_4$), perchloric acid, methyl- or ethylsulphuric acid, halogenobenzoic acids, trichloroacetic acid, and aromatic sulphonic acids such as methanesulphonic acid or p-toluenesulphonic acid. Suitable for the formation of quaternated salts of the pyrimidine derivatives of formula I wherein $R_1$ denotes a trialkylammonioalkyl radical are the corresponding anions of inorganic or organic acids of the mentioned type, as well as weak acids such as naphthoic acid, benzoic acid, acetic acid, aminoacetic acid, propionic acid, halogenopropionic acid, aliphatic dicarboxylic acids, e.g. oxalic acid, tartaric acid or maleic acid.

Preferred compounds are compounds of formula I and their salts wherein $R_1$ represents an alkyl radical having 2 to 6 carbon atoms, a cycloalkyl radical having 3 to 5 carbon atoms, or an alkenyl or alkinyl radical having 3 to 4 carbon atoms, $R_2$ represents hydrogen, $R_3$ represents hydrogen or a methyl group, $R_4$ represents hydrogen, the methyl, ethyl or isopropyl group, and $R_5$ represents a methyl or ethyl group.

Particularly important compounds as pre-emergent herbicides are the representative compounds of formula I and their salts wherein $R_1$ represents branches alkyl groups having 3 to 5 carbon atoms, $R_2$ and $R_3$ represent hydrogen, $R_4$ represents the ethyl or isopropyl group, and $R_5$ represents a methyl group.

The active substances contained in the agents according to the invention influence plant growth in different ways. Principally, they inhibit, retard or prevent germination. As already mentioned, the pyrimidine derivatives of formula I in the normally applied amounts are practically nonphytotoxic towards the emerged plants; the said active substances do, however, inhibit growth in height in the case of various species of plants. With very high dosage amounts exceeding 10 kg of AS per hectare, the plants can be damaged in differing ways also after emergence, and may even wither. The active substances of formula I also have fungicidal activity, especially phytofungicidal activity.

The new agents are particularly suitable for the treatment of corn and of lawns. With regard to corn, the growth in height is reduced, without any reduction in crop yield being observed. If, for example, emerged plants in the form of summer wheat, rye, oats and rice (plants in the 2-leaf stage) are treated with 0.05% dispersions of the following active substances:

2-methylthio-4-ethylamino-5-nitro-6-methylamino-pyrimidine,
2-methylthio-4-isopentylamino-5-nitro-6-methylamino-pyrimidine,
2-methylthio-4,6-bis-ethylamino-5-nitro-pyrimidine,
2-methylthio-4-cyanomethylamino-5-nitro-6-ethylamino-pyrimidine, 2-methylthio-4-tert.butylamino-5-nitro-6-ethylamino-pyrimidine,
2-methylthio-4-(2'-pentylamino)-5-nitro-6-ethylamino-pyrimidine,
2-methylthio-4-(3'-pentylamino)-5-nitro-6-ethylamino-pyrimidine,
2-methylthio-4-(sec.butylamino)-5-nitro-6-isopropylamino-pyrimidine,
2-methylthio-4-propylamino-5-nitro-6-isopropylamino-pyrimidine,
2-methylthio-4-ethylamino-5-nitro-6-[3'-(2',4'-dimethyl)-pentylamino]-pyrimidine,
2-methylthio-4-ethylamino-5-nitro-6-[2'-(3'-methyl)-pentylamino]-pyrimidine,
2-methylthio-4,6-bis-(isopropylamino)-5-nitro-pyrimidine,
2-methylthio-4-ethylamino-5-nitro-6-n-propylamino-pyrimidine,
2-methylthio-4-ethylamino-5-nitro-6-sec-butylamino-pyrimidine,
2-methylthio-4-ethylamino-5-nitro-6-cyclopropylamino-pyrimidine,
2-methylthio-4-ethylamino-5-nitro-6-isoamylamino-pyrimidine,
2-methylthio-4-ethylamino-5-nitro-6-allylamino-pyrimidine,
2-methylthio-4-dimethylamino-5-nitro-6-cyclopropylamino-pyrimidine,
2-methylthio-4-isopropylamino-5-nitro-6-(3'-pentylamino)-pyrimidine, then a 50–60% retardation of growth in height is obtained after 21 days. The plants are strong and dark green in colour. Similar results are obtained in the case of ornamental plants, e.g. Impatiens spp., and in the case of soya bean, with application of 0.1% dispersions of active substance. The condition of the test plants is likewise very good. With the treatment of existing cultivated lawns, the growth in height of the lawn grasses is retarded and tillering increased. Weeds in lawns, such as, e.g. Poa annua, dandelion, species of plantain, thistles, etc., which vigorously and rapidly run to seed, are very intensively checked and thus effectively removed from cultivated lawns. With a lawn mixture consisting of Poa pratensis, Festuca ovina, Festuca rubea and Lolium, the reduction in height is between 30 and 70% (applied amount = 5 kg per hectare).

Furthermore, the new active substances or corresponding agents can be employed also as agents for regulating growth, for the reduction of fruit setting, for the thinning of fruit crops, for fruit abscission or for the retardation of blossoming, and, moreover, as agents for effecting defoliation or for the prevention of undesirable side shoots (e.g. in the case of tomato plants, tabacco plants, ornamental plants, grape vines, etc.). To be emphasised, in particular, is the use of the new active substances for the prevention of sprouting in the case of stored tubers, e.g. in the case of ornamental plant bulbs, potatoes, or onions. In small doses, nitropyrimidines of formula I impart to a treated plant a greater degree of insensitivity to dryness, to frost and to a higher salt content in the soil.

In particular, the new agents can be employed, however, as pre-emergent herbicides in the most diverse of cultivated crops, such as corn, maize, rice, cotton, soya beans, sorghum, sugar beet, potatoes, beans, groundnuts, etc.. The amounts applied differ and are dependent on the time of application. They are between 0.1 and 5 kg of active substance per hectare in the case of application before emergence of the plants, and, preferably, up to 4 kg per hectare for the treatment of existing cultivated lawns. An amount of usually up to 5 kg per hectare is applied to prevent weed infestation, e.g. of railway embankments, factory sites, streets, etc..

Herbicidal action with application of the active substances before emergence of the plants (pre-emergence application)

a. The active substances are mixed with compost soil in a concentration of 60 mg of active substance per liter of soil. The following test plants are sown in this soil (seed trays):
Solanum Lycopersianum,
Setaria italica,
Avena sativa,
Lolium perenne,
Sinapis alba.

The seed trays are subsequently maintained at 22° to 25° with 50 to 70% humidity in a greenhouse. The test results are evaluated after 20 days. The evaluation is made on the basis of the following scale of values:
1 = plants destroyed,
2–4 = intermediate stages of damage,
9 = plants undamaged (control),
- = not tested.

| Active Substance | Solanum Lycopers | Setaria italica | Avena sativa | Lolium perenne | Sinapis alba | Vicia sativa | Stellaria media |
|---|---|---|---|---|---|---|---|
| 2-Methylthio-4,6-bis-propylamino-5-nitro-pyrimidine | 5 | 2 | 5 | 2 | 3 | — | — |
| 2-Methylthio-4-ethylamino-5-nitro-6-amino-pyrimidine | 2 | 1 | 3 | 1 | 2 | — | — |
| 2-Methylthio-4-isopropylamino-5-nitro-6-methylamino-pyrimidine | 3 | 2 | 4 | 3 | 3 | — | — |
| 2-Methylthio-4-sec-butylamino-5-nitro-6-methylamino-pyrimidine | 3 | 2 | 4 | 4 | 4 | — | — |
| 2-Methylthio-4,6-bis-cyclopropylamino-5-nitro-pyrimidine | 2 | 2 | 2 | 2 | 2 | — | — |
| 2-Methylthio-4-ethylamino-5-nitro-6-dimethylamino-pyrimidine | 2 | 2 | 2 | 2 | 2 | — | — |
| 2-Methylthio-4-isopropylamino-5-nitro-6-dimethylamino-pyrimidine | 2 | 1 | 2 | 1 | 3 | — | — |
| 2-Methylthio-4-isobutylamino-5-nitro-6-dimethylamino-pyrimidine | 2 | 2 | 3 | 5 | 4 | — | — |
| 2-Methylthio-4,6-bis-sec-butylamino-5-nitro-pyrimidine | 4 | 2 | 5 | 2 | — | — | — |
| 2-Methylthio-4-ethylamino-5-nitro-6-sec. butylamino-pyrimidine | 2 | 1 | 2 | 1 | 2 | 2 | — |
| 2-Methylthio-4-ethylamino-5-nitro-6-(pentyl-3'-amino-pyrimidine | 2 | 1 | 2 | 2 | 2 | — | 1 |

-continued

| Active Substance | Solanum Lycopers | Setaria italica | Avena sativa | Lolium perenne | Sinapis alba | Vicia sativa | Stellaria media |
|---|---|---|---|---|---|---|---|
| 2-Methylthio-4-isopropylamino-5-nitro-6-(pentyl-3'-amino)pyrimidine | 3 | 1 | 2 | 1 | 4 | — | 1 | b. Immediately after the sowing of the test plants, the active substances are applied as an aqueous suspension, obtained from a 25% wettable powder, to the surface of the soil. The seed trays are then maintained at 22° – 23° with 50 – 70% relative humidity. The results of the test are assessed after 28 days. The following were used as test plants:

Weeds: Poa trivialis,
Lolium multiflorum,
Alopecurus myosuorides,
Digitaria sanguinalis,
Amaranthus docendens,
Setaria italica,
Echinochloa crus galli,
Rottboellia exelt.

Cultivated plants: soya bean (*Glycine hyspida*),
cotton (*Gossypium herbaccara*),
maize (*Zea Mais*),
wheat (*Triticum vulgare*),
oats (*Avena sativa*),
rice (*Oryza*),
sugar beet (*Beta*),
sorghum (*Sorghum hybridum*).

The respective amounts applied in this test are shown in the following tables. The evaluation is on the basis of the scale of values given under Test a.

| Active substance: | Applied amount in kg/hectare | Poa trivialis | Lolium multiflorum | Alopecurus myosuorides | Digitaria sanguinalis | Amaranthus docendens | Setaria italica | Echinochloa crus galli | Rottboellia exelt. |
|---|---|---|---|---|---|---|---|---|---|
| 2-Methylthio-4,6-bis-isopropylamino-5-nitro-pyrimidine | 4 | 1 | 2 | 2 | 1 | 2 | 2 | 2 | — |
|  | 2 | 1 | 2 | 2 | 2 | 2 | 3 | 2 | — |
|  | 1 | 1 | 5 | — | 2 | 5 | 4 | 3 | — |
| 2-Methylthio-4-sec-butylamino-5-nitro-6-ethylamino-pyrimidine | 4 | 1 | 2 | 2 | 1 | 2 | 2 | 2 | — |
|  | 2 | 1 | 3 | 3 | 2 | 2 | 2 | 2 | — |
|  | 1 | 1 | 3 | 5 | 2 | 2 | 2 | 2 | — |
| 2-Methylthio-4-ethylamino-5-nitro-6-cyclopropylamino-pyrimidine | 4 | 1 | 1 | 2 | 2 | 2 | 2 | 2 | — |
|  | 2 | 1 | 2 | 3 | 2 | 2 | 2 | 2 | — |
|  | 1 | 2 | 4 | 5 | 3 | 2 | 3 | 5 | — |
| 2-Methylthio-4-isopropylamino-5-nitro-6-ethylamino-pyrimidine | 4 | 1 | 1 | 2 | 3 | 2 | — | — | — |
|  | 2 | 1 | 2 | 4 | 4 | 3 | — | — | — |
|  | 1 | — | 5 | — | 5 | 4 | — | — | — |
| 2-Methylthio-4,6-bis-ethylamino-5-nitro-pyrimidine | 4 | 1 | 2 | 2 | 2 | 2 | — | — | — |
|  | 2 | 1 | 3 | 3 | 2 | 3 | — | — | — |
|  | 1 | 1 | 5 | 3 | 3 | 4 | — | — | — |
| 2-Methylthio-4-propylamino-5-nitro-6-ethylamino-pyrimidine | 4 | 1 | 2 | 2 | — | 2 | — | — | — |
|  | 2 | 1 | 2 | 3 | — | 2 | — | — | — |
|  | 1 | 5 | 5 | 4 | — | 3 | — | — | — |
| 2-Methylthio-4-ethylamino-5-nitro-6-methylamino-pyrimidin | 4 | 1 | — | — | 2 | 2 | 2 | — | — |
|  | 2 | 1 | — | — | 2 | 2 | 2 | — | — |
|  | 1 | 3 | — | — | 5 | 5 | 3 | — | — |
| 2-Methylthio-4-ethylamino-5-nitro-6-(pentyl-3'-amino)-pyrimidine | 4 | — | 2 | 1 | 1 | 1 | 1 | 1 | 2 |
|  | 2 | — | 5 | 1 | 1 | 1 | 1 | 1 | 8 |
|  | 1 | — | 8 | 2 | 1 | 1 | 1 | 1 | 8 |
| 2-Methylthio-4-isopropylamino-5-nitro-6-(pentyl-3'-amino)-pyrimidine | 4 | — | 2 | 2 | 1 | 1 | 1 | 1 | 1 |
|  | 2 | — | 2 | 2 | 2 | 2 | 1 | 1 | 2 |
|  | 1 | — | 4 | 2 | 2 | 2 | 2 | 1 | 2 |

| Active substance: | Applied amount kg/hect. | Soya bean | Cotton | Maize | Wheat | Oats | Dry rice | Sugar beet |
|---|---|---|---|---|---|---|---|---|
| 2-Methylthio-4,6-bis-isopropyl-amino-5-nitro-pyrimidine | 4 | 9 | 9 | — | 8 | — | — | — |
|  | 2 | 9 | 9 | — | 8 | — | — | — |
|  | 1 | 9 | 9 | — | 9 | — | — | — |
| 2-Methylthio-4-sec-butylamino-5-nitro-6-ethylamino-pyrimidine | 4 | 9 | 9 | — | — | 8 | 7 | — |
|  | 2 | 9 | 9 | 8 | — | 9 | 7 | — |
|  | 1 | 9 | 9 | 8 | 8 | 9 | 8 | 6 |
| 2-Methylthio-4-ethylamino-5-nitro-6-cyclopropylamino-pyrimidine | 4 | 8 | 9 | 8 | 8 | 8 | — | — |
|  | 2 | 9 | 9 | 8 | 9 | 9 | — | — |
|  | 1 | 9 | 9 | 9 | 9 | 9 | — | — |
| 2-Methylthio-4-isopropylamino-5-nitro-6-ethylamino-pyrimidine | 4 | 8 | 8 | 7 | 8 | 7 | — | — |
|  | 2 | 9 | 9 | 8 | 9 | 8 | — | — |
|  | 1 | 9 | 9 | 8 | 9 | 9 | — | — |
| 2-Methylthio-4,6-bis-ethylamino-5-nitro-pyrimidine | 4 | 9 | 8 | 8 | 7 | 8 | — | — |
|  | 2 | 9 | 9 | 8 | 8 | 8 | — | — |
|  | 1 | 9 | 9 | 9 | 8 | 8 | — | — |
| 2-Methylthio-4-propylamino-5-nitro-ethylamino-pyrimidine | 4 | 7 | 7 | 7 | 8 | — | — | — |
|  | 2 | 8 | 8 | 8 | 9 | — | — | — |
|  | 1 | 9 | 8 | 8 | 9 | — | — | — |
| 2-Methylthio-4-ethylamino-5-nitro-6-methylamino-pyrimidine | 4 | 9 | 9 | 7 | 7 | 7 | — | — |
|  | 2 | 9 | 9 | 7 | 9 | 8 | — | — |
|  | 1 | 9 | 9 | 8 | 9 | 9 | — | — |
| 2-Methylthio-4-ethylamino-5-nitro-6-(pentyl-3'-amino)- | 4 | 8 | 9 | 7 | 8 | 8 | — | — |
|  | 2 | 8 | 9 | 8 | 8 | 7 | 8 | — |

-continued

| Active substance: | Applied amount kg/hect. | Soya bean | Cotton | Maize | Wheat | Oats | Dry rice | Sugar beet |
|---|---|---|---|---|---|---|---|---|
| pyrimidine | 1 | 9 | 9 | 9 | 9 | 8 | 8 | 7 |
| 2-Methylthio-4-isopropylamino- | 4 | 7 | 7 | — | — | — | — | — |
| 5-nitro-6-(pentyl-3'-amino)- | 2 | 7 | 7 | 6 | 7 | — | — | 6 |
| pyrimidine | 1 | 7 | 9 | 7 | 7 | 7 | 5 | 8 |

Also the following compounds are tested by the procedure described under Method b. In the following table, the values for the degree of effectiveness with applied amounts of 4 kg of A.S./hectare appear before the comma, and the values with applied amounts of 2 kg of A.S./hectare after the comma.

| Compound No. | Beta Sugar beet | Cotton | Soja Glycine | Water rice Oryza | Dry rice Oryza | Sorghum hybridum | Maize Zea | Wheat Triticum | Oats Avena | Poa trivialis | Lolium multiflorum | Alopecurus myos. | Digitaria sanguin. | Amaranthus spez. | Setaria italica | Echinochloa crusgalli | Rottboellia exelt. |
|---|---|---|---|---|---|---|---|---|---|---|---|---|---|---|---|---|---|
| 4 | 8,8 | 7,8 | 7,8 | 3,6 | 8,7 | 7,8 | 7,8 | 8,9 | 3,4 | 1,1 | 2,2 | 2,3 | 3,3 | 2,2 | 3,4 | 3,7 | — |
| 6 | 9,9 | —,— | 9,9 | 8,9 | 9,9 | —,8 | 9,9 | 8,8 | 8,8 | 3,9 | 9,9 | 8,8 | 3,3 | 5,7 | 2,7 | 2,3 | — |
| 9 | 8,9 | 8,8 | 8,8 | 8,9 | 8,9 | 7,8 | 8,9 | 8,9 | 8,9 | — | 9,9 | 2,2 | 1,2 | 2,2 | 1,1 | 1,3 | — |
| 10 | 7,7 | — | 9,9 | 8,9 | 8,9 | 8,9 | 9,9 | 9,9 | 9,9 | 5,6 | 8,9 | 6,7 | 3,8 | 3,4 | 8,8 | 4,7 | — |
| 12 | 9,9 | 9,9 | 12,8 | 3,4 | 7,7 | 2,8 | 8,8 | 9,9 | 9,9 | 1,1 | 3,8 | 1,2 | 1,1 | 2,2 | 2,3 | 2,2 | — |
| 15 | 4,7 | 8,9 | 8,9 | 6,6 | 8,9 | 8,9 | 6,8 | 8,9 | 7,8 | 1,1 | 1,2 | 2,4 | 3,4 | 2,3 | 2,7 | 1,5 | — |
| 22 | 9,9 | 2,7 | 6,6 | 9,9 | 9,9 | 8,9 | 8,9 | 9,9 | 9,9 | 1,3 | 9,9 | 9,9 | 2,2 | 2,2 | 2,2 | 2,2 | — |
| 23 | 9,9 | 5,5 | 6,7 | 9,9 | 9,9 | 9,9 | 9,9 | 9,9 | 9,9 | 2,3 | 7,8 | 9,9 | 2,2 | 2,7 | 2,7 | 2,2 | — |
| 25 | 9,9 | 9,9 | 9,9 | 4,8 | 9,9 | 6,7 | 9,9 | 8,8 | 8,8 | 1,2 | 8,8 | 3,6 | 2,5 | 3,3 | 2,7 | 2,6 | — |
| 26 | 8,8 | 8,9 | 8,9 | 8,9 | 8,9 | 7,7 | 8,8 | 8,9 | 9,9 | 6,6 | 8,9 | 7,7 | 2,7 | 4,6 | 6,7 | 2,8 | — |
| 27 | 9,9 | 9,9 | 9,9 | 9,9 | 9,9 | 8,8 | 8,8 | 9,9 | 9,9 | 3,5 | 9,9 | 8,8 | 3,4 | 3,4 | 2,6 | 2,7 | — |
| 28 | 8,8 | 9,9 | 8,8 | 8,9 | 9,9 | 7,9 | 8,9 | 8,9 | 8,9 | 7,9 | 9,9 | 8,8 | 1,7 | 2,3 | 2,7 | 3,7 | — |
| 29 | 3,3 | 9,9 | 2,4 | 2,3 | 7,7 | 2,3 | 8,9 | 9,9 | 9,9 | 1,1 | 1,3 | 1,1 | 1,1 | 2,2 | 1,1 | 2,4 | — |
| 30 | 3,7 | 9,9 | 2,8 | 7,8 | 8,9 | 9,9 | 3,8 | 8,9 | 8,9 | 1,1 | 9,9 | 2,2 | 1,1 | 2,2 | 1,2 | 2,6 | — |
| 31 | 9,9 | 8,9 | 9,9 | 9,9 | 9,9 | 9,9 | 9,9 | 9,9 | 9,9 | 1,1 | 8,9 | 2,2 | 1,2 | 3,8 | 2,3 | 2,3 | — |
| 32 | 9,9 | 9,9 | 9,9 | 8,8 | 8,8 | 9,9 | 7,8 | 8,9 | 9,9 | 1,2 | 9,9 | 2,3 | 2,3 | 6,8 | 2,3 | 1,2 | — |
| 33 | 9,9 | 8,9 | 9,9 | 7,9 | 8,9 | 8,8 | 9,9 | 9,9 | 9,9 | 1,7 | 9,9 | 3,8 | 2,8 | 5,8 | 2,7 | 1,4 | — |
| 38 | 9,9 | 9,9 | 9,9 | 3,7 | 3,8 | 2,3 | 5,6 | 8,9 | 3,4 | 1,1 | 2,2 | 2,2 | 1,2 | 2,5 | 2,3 | 2,2 | — |
| 45 | 2,9 | 9,9 | 9,9 | 5,5 | 2,3 | 6,8 | 9,9 | 8,8 | 8,8 | 1,1 | 1,2 | 2,2 | 1,1 | 1,1 | 2,3 | 2,2 | — |
| 47 | 4,9 | 9,9 | 9,9 | 7,8 | 9,9 | 8,9 | 8,9 | 9,9 | 9,9 | 2,6 | 9,9 | 2,7 | 2,7 | 7,9 | 7,9 | 1,8 | — |
| 48 | 9,9 | 9,9 | 9,9 | 6,6 | 7,8 | 9,9 | 8,9 | 9,9 | 9,9 | — | 9,9 | 9,9 | 1,1 | 2,3 | 2,2 | 1,2 | — |
| 49 | 3,8 | 9,9 | 9,9 | 4,7 | 7,8 | 7,7 | 8,9 | 8,9 | 4,8 | — | 2,3 | 2,3 | 1,1 | 1,2 | 1,1 | 1,1 | 7,8 |
| 52 | 7,7 | 9,9 | 8,9 | 2,4 | 8,8 | 2,2 | 2,5 | 8,9 | 6,7 | — | 7,2 | 1,1 | 1,1 | 2,2 | 1,1 | 1,1 | — |
| 53 | 9,9 | 7,8 | 8,8 | 7,8 | 4,8 | 8,8 | 9,9 | 9,9 | 8,8 | — | 9,9 | 1,1 | 1,1 | 2,2 | 2,2 | 2,2 | — |
| 54 | 9,9 | 7,8 | 9,9 | 6,7 | 7,9 | 8,8 | 9,9 | 8,9 | 8,9 | — | 9,9 | 1,2 | 1,1 | 2,3 | 1,2 | 1,1 | — |
| 55 | 9,9 | 9,9 | 8,9 | 6,8 | 8,8 | 7,8 | 9,9 | 9,9 | 9,9 | — | 8,8 | 2,2 | 2,2 | 6,6 | 3,7 | 2,7 | — |
| 56 | 8,8 | 8,8 | 9,9 | 7,8 | 7,7 | 8,8 | 8,9 | 9,9 | 8,9 | — | 9,9 | 2,3 | 2,3 | 4,9 | 2,4 | 2,3 | — |
| 57 | 7,8 | 9,9 | 9,9 | 3,7 | 4,9 | 7,8 | 9,9 | 9,9 | 9,9 | — | 9,9 | 1,2 | 2,4 | 2,2 | 2,2 | 1,2 | — |
| 58 | 3,7 | 7,8 | 9,9 | 4,7 | 8,8 | 7,8 | 8,9 | 9,9 | 9,9 | — | 9,9 | 1,1 | 1,2 | 1,2 | 1,2 | 1,2 | — |
| 59 | 9,9 | 9,9 | 8,9 | 8,9 | 7,8 | 9,9 | 8,9 | 9,9 | 9,9 | — | 9,9 | 8,9 | 1,2 | 9,9 | 4,4 | 2,7 | — |
| 60 | 8,9 | 9,9 | 8,8 | 8,9 | 8,9 | 8,9 | 9,9 | 9,9 | 9,9 | — | 9,9 | 2,9 | 1,1 | 8,9 | 2,2 | 3,5 | — |
| 61 | 8,8 | 9,9 | 8,9 | 7,8 | 7,9 | 9,9 | 9,9 | 8,9 | 9,9 | — | 8,9 | 3,7 | 1,1 | 3,4 | 1,1 | 2,4 | — |
| 62 | 7,8 | 8,2 | 8,8 | 7,8 | 8,9 | 7,8 | 8,8 | 7,9 | 2,8 | — | 2,8 | 3,3 | 1,2 | 4,5 | 2,4 | 1,6 | — |
| 66 | 8,8 | 9,9 | 8,9 | 3,6 | 6,4 | 8,8 | 8,9 | 8,9 | 7,9 | — | 4,7 | 3,7 | 1,1 | 2,2 | 1,2 | 1,1 | 7,7 |
| 76 | 9,9 | 7,9 | 9,9 | 8,9 | 9,9 | 9,9 | 8,9 | 9,9 | 9,9 | — | 8,9 | 9,9 | 1,1 | 2,3 | 1,3 | 9,9 | 9,9 |
| 81 | 4,4 | 9,9 | 9,9 | 9,9 | 8,9 | 8,9 | 8,9 | 9,9 | 9,9 | — | 8,8 | 9,9 | 1,2 | 2,2 | 3,3 | 9,9 | 3,9 |

Herbicidal agents according to the invention are produced in a manner known per se by the intimate mixing and grinding of active substances of the general formula I with suitable carriers, optionally with the addition of dispersing agents or solvents which are inert to the active substances. The active substances can be obtained and used in the following forms:
solid preparations: dusts, scattering agents, granulates, (coated granulates, impregnated granulates and homogeneous granulates);
water-dispersible concentrates of the active substance: wettable powders, pastes, emulsions;
liquid preparations: solutions.

The solid preparations (dusts, scattering agents, granulates) are produced by the mixing of the active substances with solid carriers. Suitable carriers are, e.g. kaolin, talcum, bole, loess, chalk, limestone, ground limestone, Attaclay, dolomite, diatomaceous earth, precipitated silicic acid, alkaline-earth silicates, sodium and potassium aluminium silicates (feldspar and mica), calcium and magnesium sulphates, magnesium oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., alone or in admixture with each other.

The particle size of the carriers is for dusts advantageously up to about 0.1 mm; for scattering agents from about 0.075 mm to 0.2 mm; and for granulates 0.2 mm or coarser.

The concentrations of active substance in the solid preparation forms are from 0.5 to 80%.

To these mixtures may also be added additives stabilising the active substance, and/or non-ionic, anionactive, and cation-active substances, which, for example, improve the adhesiveness of the active substances on plants and on parts of plants (adhesives and agglutinants), and/or ensure a better wettability (wetting agents) and dispersibility (dispersing agents). Suitable adhesives are, for example, the following: olein/chalk mixture, cellulose derivatives (methyl cellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, its alkali metal and alkaline-earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of ethylene oxide, propylene oxide, polyvinyl pyrrolidones, polyvinyl alcohols, condensation products of urea and formaldehyde, as well as latex products.

Water-dispersible concentrates of active substance, i.e. wettable powders, pastes and emulsion concentrates, are agents which can be diluted with water to obtain any desired concentration. They consist of active substance, carrier, optionally additives which stabilise the active substance, surface-active substances, and anti-foam agents and, optionally, solvents. The concentration of active substance in these agents is 5 to 80%.

The wettable powders and the pastes are obtained by the mixing and grinding of the active substances with dispersing agents and pulverulent carriers, in suitable devices, until homogeneity is attained. Suitable carriers are, e.g. those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formaldehyde, condensation products of naphthalene or of naphthalenesulphonic acids with phenol and formaldehyde, as well as alkali, ammonium and alkaline-earth metal salts of ligninsulphonic acid, also alkylaryl sulphonates, alkali metal salts and alkaline-earth metal salts of dibutyl naphthalenesulphonic acid, fatty alcohol sulphates such as salts of sulphated hexadecanols, heptadecanols, octadecanols, and salts of sulphated fatty alcohol glycol ether, the sodium salt of oleyl methyl tauride, ditertiary acetylene glycols, dialkyl dilauryl ammonium chloride, and fatty acid alkali-metal and alkaline-earth metal salts.

Suitable anti-foam agents are, for example, silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. Dispersing agents such as those mentioned in the preceding paragraphs, organic solvents and water are used in the preparation of emulsion concentrates and pastes. Suitable solvents are, e.g. the following: alcohols, benzene, xylenes, toluene, dimethylsulphoxide, N,N-dialkylated amides, N-oxides of amines, especially trialkylamines, and mineral oil fractions boiling in the range of 120° to 350°. The solvents must be practically odourless, non-phytotoxic, inert to the active substances, and not readily inflammable.

Furthermore, the agents according to the invention can be used in the form of solutions. For this purpose the active substance (or several active substances) is (or are) dissolved in suitable organic solvents, mixtures of solvents, water, or mixtures of organic solvents with water. As organic solvents it is possible to use aliphatic and aromatic hydrocarbons, their chlorinated derivatives, alkylnaphthalenes, mineral oils on their own or in admixture with each other. The solutions should contain the active substances in a concentration of from 1 to 20%. These solutions can be applied either with the aid of a propellent gas (as a spray), or with special spraying devices (such as aerosol).

Other biocidal active substances or agents may be added to the described agents according to the invention. For the widening of their sphere of action, the new agents may also contain, in addition to the stated compounds of the general formula I, e.g. insecticides, fungicides, bactericides, fungistatics, bacteriostatics or nematocides. The agents according to the invention can also contain fertilisers, trace elements, etc..

Preparations of the new active substances of the general formula I are described in the following. The term 'parts' denotes parts by weight.

Granulate

The following substances are used for the preparation of a 5% granulate:

5 parts of 2-methylthio-4-ethylamino-5-nitro-6-sec.-butylamino-pyrimidine,
0.25 parts of epichlorohydrin,
0.25 parts of cetyl polyglycol ether,
3.50 parts of polyethylene glycol,
91 parts of kaolin (particle size 0.3 to 0.8 mm).

The active substance is mixed with epichlorohydrin and the mixture dissolved in 6 parts of acetone; polyethylene glycol and cetyl polyglycol ether are thereupon added to the solution. The solution obtained in this manner is sprayed on to kaolin, and subsequently evaporated in vacuo.

Wettable powder

The following constituents are used for the preparation of a. a 50%, b. a 25%, and c. a 10% wettable powder:

a. 50 parts of 2-methylthio-4-ethylamino-5-nitro-6-(pent-3'-ylamino)-pyrimidine,
   5 parts of sodium dibutylnaphthyl sulphonate,
   3 parts of naphthalenesulphonic acid/phenolsulphonic acid/formaldehyde condensate 3:2:1,
   20 parts of kaolin,
   22 parts of Champagne chalk;

b. 25 parts of 2-methylthio-4-isopropylamino-5-nitro-6-methylamino-pyrimidine,
   5 parts of the sodium salt of oleylmethyl tauride,
   2.5 parts of naphthalenesulphonic acid/formaldehyde condensate,
   0.5 parts of carboxymethyl cellulose,
   5 parts of neutral potassium aluminium silicate,
   62 parts of kaolin;

c. 10 parts of 2-methylthio-4-sec.butylamino-5-nitro-6-methylamino-pyrimidine,
   3 parts of a mixture of the sodium salts of saturated fatty alcohol sulphates,
   5 parts of naphthalenesulphonic acid/formaldehyde condensate,
   82 parts of kaolin.

The stated active substance is absorbed onto the corresponding carriers (kaolin and chalk), and the whole subsequently mixed and ground. Wettable powders having excellent wettability and suspension properties are thus obtained. From such wettable powders can be obtained, by dilution with water, suspensions of any desired concentration of active substance. Such suspensions are used for the control of weeds and wild grasses in cultivated crops by the pre-emergence process, and for the treatment of lawns.

Paste

The following substances are used for the preparation of a 45% paste:

45 parts of 2-methylthio-4-isopropylamino-5-nitro-6-(pent-3′-yl-amino)-pyrimidine,
5 parts of sodium aluminium silicate,
14 parts of cetyl polyglycol ether having 8 moles of ethylene oxide,
1 part of oleylpolyglycol ether having 5 moles of ethylene oxide,
2 parts of spindle oil,
10 parts of polyethylene glycol,
23 parts of water.

The active substance is intimately mixed and ground, in suitable devices, with the additives. A paste is thus obtained from which can be produced, by dilution with water, suspensions of any desired concentration.

Emulsion concentrate

The following ingredients are mixed together for the preparation of a 25% emulsion concentrate:
25 parts of 2-methylthio-4-ethylamino-5-nitro-6-dimethylamino-pyrimidine,
5 parts of a mixture of nonylphenolpolyoxyethylene and calcium dodecylbenzenesulphonate,
35 parts of 3,5,5-trimethyl-2-cyclohexen-1-one,
35 parts of dimethylformamide.

This concentrate can be diluted with water to obtain emulsions of suitable concentrations. Such emulsions are suitable for the control of weeds in cultivated crops.

Instead of the active substance given in each of the preceding preparation examples, it is also possible to employ any other one of the compounds embraced by formula I.

The new nitropyrimidine derivatives of formula I are produced according to the present invention from a corresponding 2-alkylthio-4,6-dihalogen-5-nitropyrimidine of formula IV:

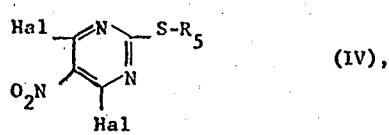

(IV), wherein $R_5$ has the meaning given under formula I, by the exchange in succession of the halogen atoms in the 4- and 6-position, preferably chlorine atoms, in the presence of an acid-binding agent, for radicals of amines of formulae II and/or III

In formulae II and III, $R_1$ to $R_4$ have the meanings given under formula I. The reaction temperatures are in the range of from −60° to +120°C, with the exchange of the 1st halogen atom being achieved between −60° and +20°C, and that of the 2nd halogen atom between 10° and 50° or higher. The stepwise exchange necessary with the introduction of different amines II or III is governed, as is known from analogous chemical processes, by temperature, time and type of solvent.

Suitable solvents or diluents for the reactions according to the invention are water, ketones such as acetone or methyl ethyl ketone, ethers and ethereal compounds such as dioxane or tetrahydrofuran, aliphatic and aromatic hydrocarbons and halogenated hydrocarbons, also nitriles such as acetonitrile, N,N-dialkylated amides such as dimethylformamide, or sulphoxides such as dimethylsulphoxide, as well as mixtures of such solvents with each other.

Acid-binding agents most suitable for the process according to the invention are inorganic bases such as alkali metal and alkaline-earth metal hydroxides, -hydrogen carbonates and -carbonates. Also suitable as organic bases, however, are tertiary amines such as trialkylamines, dialkylanilines, pyridine and pyridine bases. Moreover, the respective amine component of formula II or III, when used in excess, can serve as the acid binding agent. Sodium hydroxide or potassium hydroxide are preferred.

It is possible to isolate as intermediates, after the 1st step of the exchange reaction with an amine II or III, compounds of the formula:

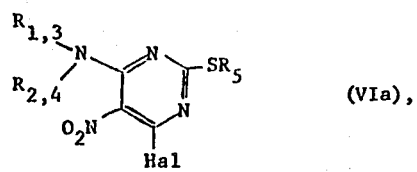

(VIa), of which a number have not yet been described in the literature.

The starting products of formula IV can be obtained, by processes known per se, by alkylation of 2-mercapto-4,6-dihydroxy-pyrimidine with a conventional alkylating agent such as alkyl halide or dialkylsulphuric acid ester, subsequent nitration of the obtained 2-alkylthio-4,6-dihydroxy-pyrimidine with nitric acid or a nitrating mixture, and substitution of the two hydroxy groups by the desired halogen atoms with the aid of phosphoryl halides such as $POCl_3$, $PCl_5$, $PBr_5$, $PCl_3$, or with thionyl chloride or thionyl bromide.

The nitropyrimidine derivatives of formula I can be produced by a further method in which, with the starting compound being 2,4,6-trihalogen-5-nitro-pyrimidine, preferably 2,4,6-trichloro-5-nitro-pyrimidine, the halogen atoms in the 4-position and in the 6-position are exchanged stepwise, in the presence of one of the above mentioned acid-binding agents, for radicals of amines of formulae II and/or III, and the halogen atom in the 2-position for the radical of a mercaptan of the formula:

(V).

The substituent $R_5$ has the meaning given in the case of formula I. Instead of the free mercaptan of formula V, it is also possible to use the alkali metal salt of this compound.

The reaction conditions of the exchange in stages correspond, in principle, to those of the 1st method. The reactions are performed in solvents or diluents inert to the reactants, such as the solvents or diluents mentioned above. The reaction temperatures are between −60° and +120°C. The stage by stage exchange of the halogen atoms is dependent on temperature, time and type of solvent. In principle, the exchange of the 1st halogen atom in the 4-position of the pyrimidine molecule occurs in the range of from −60° to +20°C, that of the 2nd halogen atom in the 6-position in the range of from 10° to 50°C, and that of the 3rd halogen atom in the range of from 30° to 120°C.

The following nitropyrimidines of formulae VIb and VIc are obtained as intermediates, which can be isolated under suitable conditions, such as are described in Examples 4 and 5:

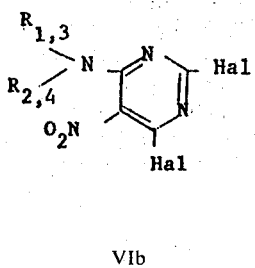

VIb

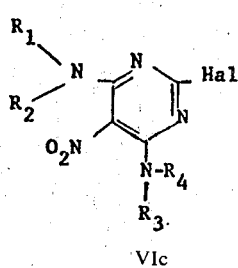

VIc

For the production of the addition salts, the pyrimidine derivatives of formula I are reacted, in a manner known per se, with inorganic and organic acids. The acids preferred for pyrimidine derivatives of formula I wherein $R_1$ has a meaning other than alkylaminoalkyl are the strong acids such as hydrohalic acids, sulphuric acid, fluoboric acid, phosphoric acids, alkylsulphuric acids, etc..

Suitable compounds for the production of quaternary salts of the new pyrimidine derivatives are, in particular, those compounds of formula I in which $R_1$ represents a dialkylaminoalkyl radical. Such pyrimidines are reacted with an alkylating agent such as, e.g. an alkyl halide or dialkylsulphates. The anion of the thus obtained ammonium salts can readily be exchanged for the anion of any desired inorganic or organic acid, this being effected:

a. by neutralisation and subsequent reaction with the corresponding acid, or
b. with the aid of an anion exchanger.

The following examples serve to illustrate the process according to the invention, and variants of the said process. The examples are followed by a list of further pyrimidine derivatives embraced by formula I together with the relevant physical data. The intermediates which have been obtained during production of the compounds of formula I are listed in a further table.

The pyrimidine derivatives given in the tables are produced analogously to the manner described in the examples.

EXAMPLE 1 a. An amount of 22.5 g of ethylamine gas is introduced with cooling, at −90° to −10°, into a solution of 120.1 g of 2-methylthio-4,6-dichloro-5-nitropyrimidine and 50.5 g of triethylamine in 2200 ml of absolute ethanol. After completion of the reaction, the mixture is concentrated by evaporation to dryness; the residue is suspended in cold water, washed, and separated. After recrystallisation from hexane, 2-methylthio-4-chloro-5-nitro-6-ethylamino-pyrimidine, M.P. 100° to 101°C, is obtained b. An amount of 10 g of sec. butylamine is added dropwise at 35° to 45° to a solution of 2-methylthio-4-chloro-5-nitro-6-ethylamino-pyrimidine in 100 ml of absolute ethanol. After 18 hours' stirring at 25°, the reaction mixture is concentrated by evaporation to dryness, and the residue extracted with ether. After drying, and removal by distillation of the ether, the residue is recrystallised from a 2 : 1 pentane/hexane mixture. The obtained 2-methylthio-4-sec.butylamino-5-nitro-6-ethylamino-pyrimidine has the M.P.: 45° – 47°C (Comp. No. 1).

EXAMPLE 2

An amount of 50 g (1.11 moles) of ethylamine gas is slowly introduced at ca. 35°C, without cooling, into a solution of 60.0 g of 2-methylthio-4,6-dichloro-5-nitropyrimidine in 750 ml of absolute ethanol. The mixture is subsequently stirred for 2 hours at room temperature, and concentrated at 45° in vacuo to dryness. The residue is suspended in 500 ml of water, separated, and washed with water. The product is recrystallised from a mixture of hexane and pentane in the ratio of 10 : 1. The obtained 2-methylthio-4,6-bis-ethylamino-5-nitropyrimidine has the M.P.: 130° – 131°C. (Compound No. 2)

Calcul.: % C: 42.01 H: 5.88 N: 27.22 S: 12.46;
Found: : % C: 42.00 H: 5.83 N: 27.17 S: 12.31

EXAMPLE 3 a. An amount of 184.1 g of n-butyliodide is added to 144.2 g of 2-mercapto-4,6-dihydroxy-pyrimidine dissolved in 1000 ml of 2-n aqueous sodium hydroxide solution, and the whole heated for 2 hours at 85°–90°C. After cooling, the reaction mixture is rendered acid, to a congo-red indicator, with ice and concentrated hydrochloric acid. The 2-n-butylthio-4,6-dihydroxy-pyrimidine obtained as a precipitate is separated and dried.

b. An amount of 20 g of 2-n-butylthio-4,6-dihydroxy-pyrimidine is slowly added, with ice/sodium chloride cooling, to 60 ml of fuming nitric acid. The reaction mixture is stirred for 30 minutes at 0°, and afterwards transferred into ice water. The brown precipitate is then separated, washed with water and dried. The obtained 2-butylthio-4,6-dihydroxy-5-nitropyrimidine has the M.P.: 155° – 157°C.

c. 110 g of 2-n-butylthio-4,6-dihydroxy-5-nitropyrimidine is heated together with 500 ml of phosphorus oxychloride to 80°, and then carefully with 146 ml of diethylaniline in such a manner that the occurring intense exothermic reaction remains controllable. The mixture is subsequently heated for 90 minutes at 150°C bath temperature and, after cooling, added to ice water. The aqueous solution is then repeatedly extracted with ether. After drying over magnesium sulphate, the ether extracts are separated from the solvent. The residue is taken up in petroleum ether and separated from the oily constituent. After the petroleum ether has been distilled off, the oil is distilled. The obtained 2-n-butylthio-4,6-dichloro-5-nitropyrimidine has the B.P.: 135° – 140°C/0.001 Torr.

d. An amount of 7.7 g of ethylamine gas is passed at 45° – 50° into the solution of 10 g of 2-n-butylthio-4,6-dichloro-5-nitropyrimidine in 100 ml of absolute ethanol. The reaction mixture is then concentrated in vacuo to dryness and the residue slurried with water. The undissolved precipitate is separated and recrystallised from hexane. The obtained 2-n-butylthio-4,6-diethylamino-5-nitropyrimidine has the M.P.: 112°C. (Compound No. 3).

EXAMPLE 4

Additions are made successively of 0.44 g of triethylamine and 0.26 g of isopropylamine, at -15° to -10°C, to a solution of 1.0 g of 2,4,6-trichloro-5-nitropyrimidine in 30 ml of diethyl ether. During a stirring time of 10 minutes, a white precipitate of triethylamine hydrochloride is obtained, which is filtered off after completion of the reaction. After concentration by evaporation of the filtrate, an amount of 800 mg of 2,4-dichloro-5-nitro-6-isopropylamino-pyrimidine is obtained which, after recrystallisation for ether/hexane, melts at 65°–70°c.

The exchange of the 2nd chlorine atom in 4-position for an amino group, and that of the 3rd chlorine atom in 2-position for a lower alkylthio group, can be performed under the conditions of Example 5.

EXAMPLE 5

An amount of 3 g of ethylamine gas is introduced at 0° into a solution of 3.7 g of 2,4,6-trichloro-5-nitropyrimidine in 50 ml of ethanol. The solution is then maintained for 30 minutes at 5° to 10°C, and subsequently concentrated at 30°C in vacuo to dryness. The residue is washed with water and dried. The obtained 2-chloro-4,6-bis-ethylamino-5-nitro-pyrimidine has the M.P.: 130°–132°C. If the ethanolic solution of 2-chloro-4,6-bis-ethylamino-5-nitro-pyrimidine is heated in the presence of sodium hydroxide and equimolar amounts of methyl mercaptan in an autoclave to 50° – 70°C, then 2-methylthio-4,6-bis-ethylamino-5-nitro-pyrimidine is obtained.

Table 1

| No. | Compounds: | Melting points in °C |
|---|---|---|
| 4 | 2-Methylthio-4-n-propylamino-5-nitro-6-ethyl-amino-pyrimidine | 114° |
| 5 | 2-Methylthio-4-ethylamino-5-nitro-6-dimethyl-amino-pyrimidine | 173–175° |
| 6 | 2-Methylthio-4-isopentylamino-5-nitro-6-ethyl-amino-pyrimidine | 26° |
| 7 | 2-Methylthio-4-ethylamino-5-nitro-6-methylamino-pyrimidine | 119–121° |
| 8 | 2-Methylthio-4-ethylamino-5-nitro-6-amino-pyrimidine | 177° |
| 9 | 2-Methylthio-4-tert.butylamino-5-nitro-6-ethyl-amino-pyrimidine | 62–64° |
| 10 | 2-Methylthio-4-(1,1dimethyl-1-cyano-methyl)-amino-5-nitro-6-ethylamino-pyrimidine | 120–122° |
| 11 | 2-Methylthio-4-ethylamino-5-nitro-6-cyclopropyl-amino-pyrimidine | 128–130° |
| 12 | 2-Methylthio-4-allylamino-5-nitro-6-ethyl-amino-pyrimidine | 110° |
| 13 | 2-Methylthio-4-sec.butylamino-5-nitro-6-dimethyl-amino-pyrimidine | 178° |
| 14 | 2-Methylthio-4-isopropylamino-5-nitro-6-dimethyl-amino-pyrimidine | 181–182° |
| 15 | 2-Methylthio-4-isopropylamino-5-nitro-6-ethyl-amino-pyrimidine | 80–81° |
| 16 | 2-Methylthio-4-sec.butylamino-5-nitro-6-methyl-amino-pyrimidine | 85–87° |
| 17 | 2-Methylthio-4-isopropylamino-5-nitro-6-methyl-amino-pyrimidine | 108–110° |
| 18 | 2-Butylthio-4-isopropylamino-5-nitro-6-ethyl-amino-pyrimidine | 76–77° |
| 19 | 2-Butylthio-4-methylamino-5-nitro-6-ethylamino-pyrimidine | 88–89° |
| 20 | 2-Methylthio-4-(3-methyl-2-butenylamino)-5-nitro-6-methylamino-pyrimidine | 60–62° |
| 21 | 2-Methylthio-4-isopentylamino-5-nitro-6-methyl-amino-pyrimidine | 60–61° |
| 22 | 2-Methylthio-4-diethylamino-5-nitro-6-ethyl-amino-pyrimidine | 67–69° |
| 23 | 2-Methylthio-4-(2-methoxy-ethylamino)-5-nitro-6-ethylamino-pyrimidine | 112° |
| 24 | 2-Methylthio-4-ethanolamino-5-nitro-6-ethyl-amino-pyrimidine | 147° |
| 25 | 2-Methylthio-4-isobutylamino-5-nitro-6-ethyl-amino-pyrimidine | 60–61° |
| 26 | 2-Methylthio-4-methylamino-5-nitro-6-n-butyl-amino-pyrimidine | 75–77° |
| 27 | 2-Methylthio-4-methylamino-5-nitro-6-n-propyl-amino-pyrimidine | 106–108° |
| 28 | 2-Methylthio-4-methylamino-5-nitro-6-cyclo-propylamino-pyrimidine | 103–105 |
| 29 | 2-Methylthio-4-ethylamino-5-nitro-6-propargyl-amino-pyrimidine | 97–99° |
| 30 | 2-Methylthio-4-dimethylamino-5-nitro-6-cyclo-propylamino-pyrimidine | 125–126° |
| 31 | 2-ethylthio-4,6-bis-isopropylamino-5-nitro-pyrimidine | 102–104° |
| 32 | 2-ethylthio-4,6-bis-ethylamino-5-nitro-pyrimidine | 87–88° |
| 33 | 2-Methylthio-4-ethylamino-5-nitro-6-hydroxy-methylamino-pyrimidine | 128–130° |
| 34 | 2-Methylthio-4-ethylamino-5-nitro-6-n-butyl-amino-pyrimidine | 58–60° |
| 35 | 2-Methylthio-4,6-bis-butylamino-5-nitro-pyrimidine | 66° |
| 36 | 2-Methylthio-4,6-bis-sec.butylamino-5-nitro-pyrimidine | 45–46° |
| 37 | 2-Methylthio-4,6-bis-propylamino-5-nitro-pyrimidine | 103° |
| 38 | 2-Methylthio-4,6-bis-isopropylamino-5-nitro-pyrimidine | 123–124° |
| 39 | 2-n-Propylthio-4,6-bis-(n-propylamino)-5-nitro-pyrimidine | 90–92° |
| 40 | 2-Methylthio-4,6-bis-cyclopentylamino-5- | 76–78° |

Table 1-continued

| No. | Compounds: | Melting points in °C |
|---|---|---|
| 41 | nitro-pyrimidine 2-Methylthio-4,6-bis-cyclopropylamino-5-nitro-pyrimidine | 155° |
| 42 | 2-Methylthio-4,6-bis-cyclohexylamino-5-nitro-pyrimidine | 105° |
| 43 | 2-Methylthio-4,6-bis-dimethylamino-5-nitro-pyrimidine | 183–184° |
| 44 | 2-Butylthio-4,6-bis-isopropylamino-5-nitro-pyrimidine | 92–93° |

| No. | Compounds: | Refractive indices and Melting points in °C |
|---|---|---|
| 2 | 2-Methylthio-4,6-bis-(ethylamino)-5-nitro-pyrimidine | 148–150° |
| 1 | 2-Methylthio-4-ethylamino-5-nitro-6-sec. butylamino-pyrimidine | 45–47° |
| 3 | 2-n-Butylthio-4,6-bis(ethylamino)-5-nitro-pyrimidine | 112° |
| 45 | 2-Methylthio-4,6-bis(ethylamino)-5-nitro-pyrimidine, p-toluenesulphonate | 117° |
| 46 | N,N,N-Trimethyl-8-[(2-methylthio-4-ethylamino-5-nitropyrimidin-6)-amino]-ethylammonium-iodide | 230–232° |
| 47 | 2-Methylthio-4-ethylamino-5-nitro-6-cyanomethylamino-pyrimidine | 177° |
| 48 | 2-Methylthio-4-ethylamino-5-nitro-6-ethylene-imino-pyrimidine | 130° |
| 49 | 2-Methylthio-4-ethylamino-5-nitro-6-sec.amylamino-pyrimidine | viscous oil $n_D^{20}$ 1.6099 |
| 50 | 2-Methylthio-4-ethylamino-5-nitro-6-(pent-3'-yl)amino-pyrimidine | M.P.: 45–47° |
| 51 | 2-Methylthio-4-ethylamino-5-nitro-6-cyclohexylamino-pyrimidine | 116–117° |
| 52 | 2-Methylthio-4-isopropylamino-5-nitro-6-sec.butylamino-pyrimidine | viscous oil $n_D^{25}$ 1.6051 |
| 53 | 2-Methylthio-4-isopropylamino-5-nitro-6-n-propylamino-pyrimidine | 68° |
| 54 | 2-Methylthio-4-ethylamino-5-nitro-6-(2',4'-dimethylpent-3'-yl)amino-pyrimidine | viscous oil $n_D^{22}$ 1.6071 |
| 55 | 2-Methylthio-4-ethylamino-5-nitro-6-(4'-methylhex-2'-yl)amino-pyrimidine | viscous oil $n_D^{22}$ 1.6072 |
| 56 | 2-Methylthio-4-ethylamino-5-nitro-6-neopentylamino-pyrimidine | 64–65° |
| 57 | 2-Methylthio-4-ethylamino-5-nitro-6-(3'-methylpent-2'-yl)amino-pyrimidine | viscous oil $n_D^{22}$ 1.6082 |
| 58 | 2-Methylthio-4-ethylamino-5-nitro-6-(2'-methylcyclopropylamino)-pyrimidine | 70–71° |
| 59 | 2-Methylthio-4-ethylamino-5-nitro-6-isohexylamino-pyrimidine | viscous oil $n_D^{22}$ 1.6065 |
| 60 | 2-Methylthio-4-ethylamino-5-nitro-6-isoheptylamino-pyrimidine | viscous oil $n_D^{22}$ 1.5973 |
| 61 | 2-Methylthio-4-ethylamino-5-nitro-6-sec.pentylamino-pyrimidine | viscous oil $n_D^{22}$ 1.6161 |
| 62 | 2-Methylthio-4-ethylamino-5-nitro-6-(2'-hydroxyprop-1'-ylamino)-pyrimidine | 96° |
| 63 | 2-Methylthio-4-ethylamino-5-nitro-6-cyclobutylamino-pyrimidine | 105–106° |
| 64 | 2-Methylthio-4-isopropylamino-5-nitro-6-(1',2'-dimethylpropylamino)-pyrimidine | viscous oil $n_D^{24.5}$ 1.6000 |
| 65 | 2-Methylthio-4-isopropylamino-5-nitro-6-(1'cyclopropyl-ethylamino)-pyrimidine | $n_D^{25}$ 1.6143 |
| 66 | 2-Methylthio-4-ethylamino-5-nitro-6-(1'-cyclopropyl-ethylamino)-pyrimidine | 57–62° |
| 67 | 2-Methylthio-4-isopropylamino-5-nitro-6-(pent-2'-ylamino)-pyrimidine | $n_D^{25}$ 1.6008 |
| 68 | 2-Methylthio-4-ethylamino-5-nitro-6-(3'-methyl-but-2'-ylamino-)-pyrimidine | 68–69° |
| 69 | 2-Methylthio-4-methylamino-5-nitro-6-(pent-2'-ylamino)-pyrimidine | $n_D^{25}$ 1.6310 |
| 70 | 2-Methylthio-4-methylamino-5-nitro-6-(1'-cyclopropyl-ethylamino)-pyrimidine | 91–93° |
| 71 | 2-Methylthio-4-isopropylamino-5-nitro-6-tert.butylamino-pyrimidine | $n_D^{25.5}$ 1.6032 |
| 72 | 2-Methylthio-4-ethylamino-5-nitro-6-(N'-methyl-sec.butylamino)-pyrimidine | oil |
| 73 | 2-Methylthio-4-ethylamino-5-nitro-6-piperidino-pyrimidine | oil |
| 74 | 2-Methylthio-4-ethylamino-5-nitro-6-(1',1'dimethyl-2'-hydroxy-hylamino)-pyrimidine | 96–98° |
| 75 | 2-Methylthio-4-ethylamino-5-nitro-6-1'-ethyl-(2'-hydroxy-ethylamino)-pyrimidine | 110–111° |
| 76 | 2-Methylthio-4-ethylamino-5-nitro-6- | |

-continued

| No. | Compounds: | Refractive indices and Melting points in °C |
|---|---|---|
| | (3'-methyl-but-2'-ylamino)-pyrimidine | 75–77° |
| 77 | 2-Methylthio-4-dimethylamino-5-nitro-6-isobutylamino-pyrimidine | 178° |
| 78 | 2-Methylthio-4-ethylamino-5-nitro-6-cyclopentylamino-pyrimidine | 80–81° |
| 79 | 2-Methylthio-4-methylamino-5-nitro-6-(pent-3'-yl-amino)-pyrimidine | 47–54° |
| 80 | 2-Methylthio-4-methylamino-5-nitro-6-cyclopentylamino-pyrimidine | 99–102° |
| 81 | 2-Methylthio-4-dimethylamino-5-nitro-6-cyclopentylamino-pyrimidine | $n_D^{24}$ 1.6412 |
| 82 | 2-Methylthio-4-dimethylamino-5-nitro-6-(pent-3'-yl-amino)-pyrimidine | 45–47° |
| 83 | 2-Methylthio-4-isopropylamino-5-nitro-6-(pent-3'-yl-amino)-pyrimidine | $n_D^{24}$ 1.6033 |
| 84 | 2-Methylthio-4-isopropylamino-5-nitro-6-cyclopentylamino-pyrimidine | 72–74° |
| 85 | 2-Methylthio-4-ethylamino-5-nitro-6-(N'-methylpiperazino)-pyrimidine | 72–74° |
| 86 | 2-Methylthio-4-ethylamino-5-nitro-6-pyrrolidino-pyrimidine | 59–61° |
| 87 | 2-Methylthio-4-ethylamino-5-nitro-6-morpholino-pyrimidine | 65–70° |
| 88 | N,N-Dimethyl-N'-[2-methylthio-4-ethylamino-5-nitropyrimidin-6]-piperazonium-iodide | 210° (decomp.) |

The following intermediates of formulae VI *a* to *c* not hitherto described were obtained in the manner described in Example 3a to c.

Table 2

| Compounds: | Physical data |
|---|---|
| 2-Methylthio-4-amino-5-nitro-6-chloropyrimidine | M.P.: 175° |
| 2-Methylthio-4-methylamino-5-nitro-6-chloro-pyrimidine | M.P.: 120–121° |
| 2-Methylthio-4-sec.butylamino-5-nitro-6-chloro-pyrimidine | M.P.: 77° |
| 2-Methylthio-4-n-propylamino-5-nitro-6-chloro-pyrimidine | M.P.: 82° |
| 2-Butylthio-4-ethylamino-5-nitro-6-chloro-pyrimidine | B.P. 145°/0,01 Torr. |
| 2-Methylthio-4-dimethylamino-5-nitro-6-chloro-pyrimidine | M.P.: 104–106° |
| 2-Methylthio-4-ethylamino-5-nitro-6-chloro-pyrimidine | M.P.: 95–97° |
| 2-Methylthio-4-isopropylamino-5-nitro-6-chloro-pyrimidine | M.P.: 84–86° |
| 2-Methylthio-4-di-n-propyl-amino-5-nitro-6-chloro-pyrimidine | M.P.: 50–51° |
| 2-Chloro-4,6-bis-isopropylamino-5-nitro-pyrimidine | M.P.: 124–126° |
| 2-Chloro-4,6-bis(ethylamino)-5-nitro-pyrimidine | M.P.: 130–132° |
| 2,4-Dichloro-5-nitro-6-isopropyl-amino-pyrimidine | M.P.: 65–70° |

The 5-nitro-pyrimidine derivatives of formulae VI a to c possess fungicidal properties. In addition to having an excellent persistent action, the new compounds have a good curative action; by virtue of this action, fungi which have already penetrated the plant tissue are destroyed after application of these active substances. The said active substances can be applied direct to plants above the soil, or to the growth substrate. On the most diverse cultivated plants, such as corn, maize, rice, vegetables, ornamental plants, fruit, grape vines, field-fruits, etc., it is possible to check or destroy with the new active substances fungus infections occurring on fruit, blossom, foliage, stalks and roots; furthermore, subsequent growth is then protected from such infections. Examples of such active substances are the compounds listed in Table 2, especially 2-methylthio-4-amino-5-nitro-6-chloropyrimidine, 2-methylthio-4-isopropylamino-5-nitro-6-chloropyrimidine, 2-methylthio-4-dimethylamino-5-nitro-6-chloropyrimidine, 2-methylthio-4-ethylamino-5-nitro-6-chloropyrimidine. The compound 2-methylthio-4-methylamino-5-nitro-6-chloro-pyrimidine has a completely effective action, applied in a concentration of 500 ppm, against Podosphaera, Plasmopara, Septoria, Puccinia, Alternaria, Botrytis, Erysiphe, Phytopthora, Uromyces, and other phytopathogenic fungi. In the case of ubiquitous fungi such as Candida, Fusarium, Aspergillus, Penicillium, Trichophyton, and other kinds, a complete destruction is achieved with limiting concentrations of between 100 and 10 ppm.

Moreover, the active substances of formulae VI a to c can be employed for the treatment of seed, fruits, tubers, etc., for protection against fungus infections.

The pyrimidine derivatives of formula I and VI a–c can be mixed in various proportions with other compounds, e.g. with other fungicides, insecticides, bactericides, fungistatics, bacteriostatics, nematicides, plant fertilisers or trace elements.

I claim:

1. A composition for the control of undesired plant growth in cultivated crops which comprises (a) as active substance, an effective growth controlling amount of a 5-nitropyrimidine of the formula

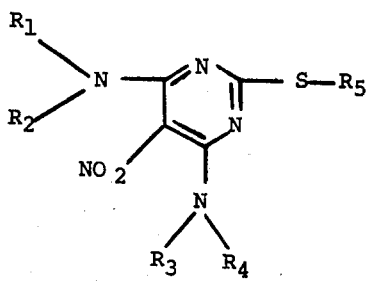

wherein
$R_1$ represents an alkyl radical having 2 to 6 carbon atoms; an alkenyl radical or alkinyl radical having 3 to 5 carbon atoms; an alkoxyalkyl, alkylaminoalkyl, or trialkylammonioalkyl radical having 1 to 6 carbon atoms in the alkyl groups thereof; a hydroxyalkyl or cyanoalkyl radical having 1 to 4 carbon atoms; or a cycloalkyl radical having 3 to 6 carbon atoms;
$R_2$ and $R_3$ each independently represent hydrogen, or a lower alkyl radical;
$R_4$ represents hydrogen, a lower alkyl radical, a cycloalkyl radical having 3 to 6 carbon atoms;
$R_5$ represents a lower alkyl radical;
together with (b) an inert carrier therefor.

2. The composition of claim 1, wherein in said 5-nitropyrimidine $R_1$ represents an alkyl radical having 2 to 6 carbon atoms, a cycloalkyl radical having 3 to 5 carbon atoms, or an alkenyl or alkinyl radical having 3 or 4 carbon atoms,
$R_2$ represents hydrogen,
$R_3$ represents hydrogen or a methyl group,
$R_4$ stands for hydrogen, the methyl, ethyl or isopropyl group, and
$R_5$ represents a methyl or an ethyl group.

3. The composition of claim 1, wherein $R_1$ represents a branched alkyl group having 3 to 5 carbon atoms,
$R_2$ and $R_3$ represent hydrogen,
$R_4$ stands for the ethyl or isopropyl group, and
$R_5$ represents a methyl group.

4. The composition of claim 3, wherein said active substance is 2-methylthio-4-ethylamino-5-nitro-6-sec. butylamino-pyrimidine.

5. The composition of claim 3, wherein said active substance is 2-methylthio-4-ehtylamino-5-nitro-6-(pent-3′-ylamino)-pyrimidine.

6. The composition of claim 3, wherein said active substance is 2-methylthio-4-isopropylamino-5-nitro-6-sec.butylamino-pyrimidine.

7. The composition of claim 3, wherein said active substance is 2-methylthio-4-isopropylamino-5-nitro-6-(pent-3′-ylamino)-pyrimidine.

8. A process for the control of undesired plant growth in cultivated crops which comprises applying to said crops prior to the emergence of said undesired plant growth an effective amount of a 5-nitropyrimidine according to claim 1.

9. The process of claim 8, wherein said 5-nitropyrimidine corresponds to the formula of claim 2.

10. The process of claim 8, wherein said 5-nitropyrimidine corresponds to the formula of claim 3.

11. The process of claim 10, wherein said 5-nitropyrimidine is 2-methylthio-4-ethylamino-5-nitro-6-sec. butylamino-pyrimidine.

12. The process of claim 10, wherein said 5-nitropyrimidine is 2-methylthio-4-ethylamino-5-nitro-6-(pent-3′-ylamino)-pyrimidine.

13. The process of claim 10, wherein said 5-nitropyrimidine is 2-methylthio-4-isopropylamino-5-nitro-6-sec.butylamino-pyrimidine.

14. The process of claim 10, wherein said 5-nitropyrimidine is 2-methylthio-4-isopropylamino-5-nitro-6-(pent-3′-ylamino)-pyrimidine.

* * * * *